United States Patent
Meng

(10) Patent No.: US 11,319,293 B2
(45) Date of Patent: May 3, 2022

(54) POLYMORPS OF CARIPRAZINE HYDROCHLORIDE AND PREPARATION METHOD THEREOF AND USE OF SAME

(71) Applicant: SHANGHAI BEGREAT PHARMATECH, Shanghai (CN)

(72) Inventor: Xiaoming Meng, Tianjin (CN)

(73) Assignee: SHANGHAI BEGREAT PHARMATECH, Shanghai (CN)

( * ) Notice: Subject to any disclaimer, the term of this patent is extended or adjusted under 35 U.S.C. 154(b) by 0 days.

(21) Appl. No.: 16/840,518

(22) Filed: Apr. 6, 2020

(65) Prior Publication Data

US 2020/0231552 A1    Jul. 23, 2020

Related U.S. Application Data

(63) Continuation of application No. PCT/CN2018/119476, filed on Dec. 6, 2018.

(30) Foreign Application Priority Data

Sep. 21, 2018   (WO) ................ PCT/CN2018/106868

(51) Int. Cl.
*C07D 241/04* (2006.01)

(52) U.S. Cl.
CPC ........ *C07D 241/04* (2013.01); *C07B 2200/13* (2013.01)

(58) Field of Classification Search
CPC .......................... C07D 241/04; C07B 2200/13

USPC ...................................................... 514/255.03
See application file for complete search history.

(56) References Cited

U.S. PATENT DOCUMENTS

| 7,943,621 B2 * | 5/2011 | Czibula ................ C07D 241/04 514/252.12 |
| 2009/0023750 A1 * | 1/2009 | Czibula ................... A61P 25/18 514/255.03 |
| 2011/0028722 A1 | 2/2011 | Liao et al. |
| 2014/0051710 A1 | 2/2014 | Liao et al. |

FOREIGN PATENT DOCUMENTS

CN           106543105 A          3/2017

OTHER PUBLICATIONS

International Search Report in PCT/CN2018/119476 dated Jun. 21, 2019, 10 pages.

* cited by examiner

*Primary Examiner* — Timothy R Rozof
(74) *Attorney, Agent, or Firm* — Metis IP LLC

(57) ABSTRACT

The present disclosure discloses crystal forms A, B, and C of trans-N-{4-[2-[4-(2,3-dichlorophenyl)-piperazine-1-yl]-ethyl]-cyclohexyl}-N',N'-dimethylurea hydrochloride, a preparation method, and a medicinal use thereof. Compared to the existing crystalline forms, the new crystalline forms have clear advantages with respect to solubility, stability, and the preparation process.

9 Claims, 9 Drawing Sheets

POLYMORPS OF CARIPRAZINE HYDROCHLORIDE AND PREPARATION METHOD THEREOF AND USE OF SAME

CROSS-REFERENCE TO RELATED APPLICATIONS

This application is a continuation of International Patent Application No. PCT/CN2018/119476 filed on Dec. 6, 2018, which claims priority to International Patent Application No. PCT/CN2018/106868, filed on Sep. 21, 2018, the entire contents of which are hereby incorporated by reference.

TECHNICAL FIELD

The present invention relates to novel crystals of trans-N-{4-[2-[4-(2,3-dichlorophenyl)-piperazine-1-yl]-ethyl]-cyclohexyl}-N',N-dimethylurea hydrochloride form A, B and C, their preparation method, and use.

BACKGROUND

As used herein, the term "Compound 1" refers to the chemical compound trans-N-{4-[2-[4-(2,3-dichlorophenyl)-piperazine-1-yl]-ethyl]-cyclohexyl}-N',N-dimethylurea hydrochloride. Compound 1 is a drug already approved by the US FDA under the trade name Vraylar. The drug was developed by Gedeon Richter. Cariprazine is a partial agonist of the dopamine D2 and D3 receptors and has high selectivity for the D3 receptor. The drug was tested in a six-week clinical trial of schizophrenia, which included 1,754 participants. According to the FDA, the results of these trials show that the drug significantly reduces the symptoms of schizophrenia compared to the placebo group. The drug has also undergone a 6-week clinical trial on the treatment of bipolar disorder. The trial included 1037 subjects and the results also showed that the drug can significantly reduce the symptoms of bipolar disorder compared with the placebo group. According to the results of clinical trials, the most common adverse effects of this drug in the treatment of schizophrenia are extrapyramidal symptoms, including tremor, speech insufficiency, and dystonia. The most common adverse effects of this drug in the treatment of bipolar disorder are also extrapyramidal symptoms, manifested by inability to sit still, indigestion, vomiting, lethargy, and restlessness. Schizophrenia and bipolar disorder are important diseases that affect people's daily lives. It is very important to have different treatments for patients with different mental illnesses, so that individualized treatment can be guaranteed for each different patient.

Cariprazine has a molecular formula of $C_{21}H_{32}Cl_2N_4O$ and a molecular weight of 427.4. The chemical structural formula of cariprazine is shown below:

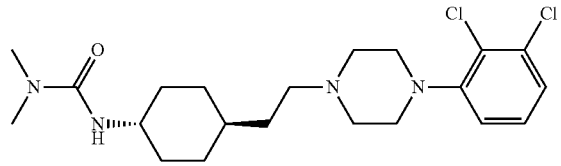 [SMILES: CN(C)C(=O)N[C@H]1CC[C@H](CCN2CCN(c3cccc(Cl)c3Cl)CC2)CC1]

Chemical raw materials of active pharmaceutical ingredients (API) must have good purity, stability, physical and chemical properties and operability. These properties are related to the crystalline form of the API. Different crystal forms have different physical and chemical properties. It is necessary to make the raw API into crystal form to improve the stability during drug storage and the efficacy of the drug.

A drug may exist in a plurality of crystalline forms, and different crystal forms of the same drug may have different performance in terms of dissolution and absorption in the body due to drug dissolution and release was controlled by crystal forms.

The optimal crystalline form can be discovered by thoroughly studying of the polymorphism of the compound. The optimal crystalline form is crucial to the drug efficacy and the formulation process which is based on the characteristics of the crystalline form, thereby effectively ensuring the equivalence of the drug batch to batch.

Drug powder flowability is also an important factor throughout the pharmaceutical formulation process. When the powder or the capsule formulation was prepared by directly mixing and filling, components are difficult to mix uniformly and affect the exact content of the drug product due to poor powder flowability. In the process of compressing or filling of granules, tablets, capsules, etc., the particles with poor flowability tend to make the surface rough of drug product or not easy to dispersible of the drug which leads to inconvenient for patients to take. Poor flowability of the drug powder also affects the smooth process and increase the cost of the drug product preparation. In the application of external powder topical formulation, the powder with poor powder flowability will lead to unevenly coated of the drug resulting in excessive or excessive topical application, which finally affecting the efficacy of the drug. In the storage and Transportation of the preparation, the formulation made of the powder with poor fluidity is more susceptible to the influence of ambient temperature, humidity, pressure, mechanical force and the like to reduce the stability and effectiveness of the drug.

Angle of repose is adopted widely to evaluate the powder flowability. When the angle of repose of the powder is less than or equal to 30 degrees, it means the flowability of this powder is good. While in case, 40 degrees or less of the powder angle of repose, this powder can satisfy the demand for fluidity in the production process. When the angle of repose of the powder is more than 40 degrees, it means the very poor flowability of the drug powder which may cause the troubles above mentioned during the drug manufacturing process.

SUMMARY

The main object of the present invention is to provide trans-N-{4-[2-[4-(2,3-dichlorophenyl)-piperazine-1-yl]-ethyl]-cyclohexyl}-N',N-dimethylurea hydrochloride new crystalline forms, and process for its preparation and medicinal use.

A crystalline form of trans-N-{4-[2-[4-(2,3-dichlorophenyl)-piperazine-1-yl]-ethyl]-cyclohexyl}-N',N'-dimethylurea hydrochloride designated as crystal form A, having an X-ray powder diffraction pattern comprising diffraction peaks at least one 2θ value of: 22.2±0.2, 18.4±0.2, 25.4±0.2, 28.2±0.2, and 24.6±0.2. Preferably, wherein the X-ray powder diffraction pattern further comprises diffraction peaks at 2θ values: 14.9±0.2, 14.3±0.2, 13.0±0.2, 20.4±0.2, 23.2±0.2, and 21.4±0.2. Preferably, wherein the X-ray powder diffraction pattern further comprises diffraction peaks at 2θ values: 31.7±0.2, 21.6±0.2, 14.0±0.2, 30.4±0.2, 26.1±0.2, or 20.7±0.2. Preferably, wherein the X-ray powder diffraction pattern further comprises diffraction peaks at 2θ values: 17.9±0.2, 17.5±0.2, 34.4±0.2, 13.7±0.2, 16.4±0.2, and 28.9±0.2. More preferably, wherein the X-ray powder diffraction pattern further comprises diffraction peaks at 2θ values: 29.7±0.2, 31.6±0.2, 27.6±0.2, 42.1±0.2, 11.0±0.2, and 44.6±0.2. More preferably, wherein the X-ray powder diffraction pattern further comprises diffraction peaks at 2θ values: 39.8±0.2, 19.2±0.2, 33.8±0.2, 33.2±0.2, 35.1±0.2, and 20.0±0.2. More preferably, wherein the X-ray powder diffraction pattern further comprises diffraction peaks at 2θ values: 40.2±0.2, 32.7±0.2, 34.0±0.2, 36.1±0.2, 31.2±0.2, and 40.4±0.2.

Trans-N-{4-[2-[4-(2,3-dichlorophenyl)-piperazine-1-yl]-ethyl]-cyclohexyl}-N',N'-dimethylurea hydrochloride Form A is anhydrous. The melting point (onset temperature) is about 198.2±2° C., which is accompanied by thermal decomposition of the sample during melting.

A process for the preparation of trans-N-{4-[2-[4-(2,3-dichlorophenyl)-piperazine-1-yl]-ethyl]-cyclohexyl}-N',N'-dimethylurea hydrochloride Form A comprising:
(i) dissolving trans-N-{4-[2-[4-(2,3-dichlorophenyl)-piperazine-1-yl]-ethyl]-cyclohexyl}-N',N'-dimethylurea free base in an organic solution. The organic solvent is selected from the group consisting of methanol, isopropanol, butyl acetate, n-hexane, acetonitrile, acetone, methyl ethyl ketone, 4-methyl-2-pentanone, diethyl ether, isopropyl ether, methyl tert-butyl ether, toluene, P-xylene, 1,2-dichloroethane, 1,4-dioxane, tetrahydrofuran, trifluorotoluene, cumene, mesitylene, chlorobenzene, n-butyl ether, methylcyclopentyl ether, Phenyl ether, 2-nitropropane, dimethyl carbonate, ethyl formate, 2-methyltetrahydrofuran, or ethylene glycol diethyl ether;
(ii) adding hydrochloride acid into the solution prepared in the step (i) to precipitate a trans-N-{4-[2-[4-(2,3-dichlorophenyl)-piperazine-1-yl]-ethyl]-cyclohexyl}-N',N'-dimethylurea chloride salt; and
(iii) trans-N-{4-[2-[4-(2,3-dichlorophenyl)-piperazine-1-yl]-ethyl]-cyclohexyl}-N',N'-dimethylurea hydrochloride Form A is obtained after liquid-solid separation.

A crystalline form of trans-N-{4-[2-[4-(2,3-dichlorophenyl)-piperazine-1-yl]-ethyl]-cyclohexyl}-N',N'-dimethylurea hydrochloride designated as crystal form B, having an X-ray powder diffraction pattern comprising diffraction peaks at at least one 2θ value of: 13.2±0.2, 17.6±0.2, 9.7±0.2, 22.6±0.2, and 19.7±0.2. Preferably, wherein the X-ray powder diffraction pattern further comprises diffraction peaks at 2θ values: 23.9±0.2, 27.1±0.2, 18.2±0.2, 15.8±0.2, and 11.8±0.2. Preferably, wherein the X-ray powder diffraction pattern further comprises diffraction peaks at 2θ values: 31.4±0.2, 24.9±0.2, and 32.7±0.2.

Trans-N-{4-[2-[4-(2,3-dichlorophenyl)-piperazine-1-yl]-ethyl]-cyclohexyl}-N',N'-dimethylurea hydrochloride Form B is anhydrous. The melting point (onset temperature) is about 230.5±2° C. There is no obvious weight lost was observed before 100° C. on the TGA plot.

A process for the preparation of trans-N-{4-[2-[4-(2,3-dichlorophenyl)-piperazine-1-yl]-ethyl]-cyclohexyl}-N',N'-dimethylurea hydrochloride Form B comprising:
(i) dissolving trans-N-{4-[2-[4-(2,3-dichlorophenyl)-piperazine-1-yl]-ethyl]-cyclohexyl}-N',N'-dimethylurea hydrochloride in an organic solution. The organic solvent is selected from the group consisting of chloroform or ethanol;
(ii) adding antisolvent (solvent has low solubility to the compound) into the solution prepared in step (i). The antisolvent was selected from N-heptane or isopropyl ether; and
(iii) trans-N-{4-[2-[4-(2,3-dichlorophenyl)-piperazine-1-yl]-ethyl]-cyclohexyl}-N',N'-dimethylurea hydrochloride Form B is obtained after liquid-solid separation.

A crystalline form of trans-N-{4-[2-[4-(2,3-dichlorophenyl)-piperazine-1-yl]-ethyl]-cyclohexyl}-N',N'-dimethylurea hydrochloride designated as crystal form C, having an X-ray powder diffraction pattern comprising diffraction peaks at at least one 2θ value of: 19.1±0.2, 16.9±0.2, 13.6±0.2, 15.8±0.2, and 4.6±0.2. Preferably, wherein the X-ray powder diffraction pattern further comprises diffraction peaks at 2θ values: 13.2±0.2, 10.9±0.2, 20.7±0.2, 19.9±0.2, and 18.1±0.2. Preferably, wherein the X-ray powder diffraction pattern further comprises diffraction peaks at 2θ values: 9.1±0.2, 12.3±0.2, and 14.9±0.2.

Trans-N-{4-[2-[4-(2,3-dichlorophenyl)-piperazine-1-yl]-ethyl]-cyclohexyl}-N',N'-dimethylurea hydrochloride Form C is anhydrous. The melting point (onset temperature) is about 165.5±2° C. There is no obvious weight lost was observed before 100° C. on the TGA plot.

A process for the preparation of trans-N-{4-[2-[4-(2,3-dichlorophenyl)-piperazine-1-yl]-ethyl]-cyclohexyl}-N',N'-dimethylurea hydrochloride Form C comprising:
(i) dissolving trans-N-{4-[2-[4-(2,3-dichlorophenyl)-piperazine-1-yl]-ethyl]-cyclohexyl}-N',N'-dimethylurea chloride salt in an organic solution. The organic solvent is selected from the group consisting of dichloromethane;
(ii) adding antisolvent (solvent has low solubility to the compound) into the solution prepared in step (i). The antisolvent was selected from N-heptane or isopropyl ether; and
(iii) obtaining trans-N-{4-[2-[4-(2,3-dichlorophenyl)-piperazine-1-yl]-ethyl]-cyclohexyl}-N',N'-dimethylurea hydrochloride Form C after liquid-solid separation.

A pharmaceutical composition may comprise trans-N-{4-[2-[4-(2,3-dichlorophenyl)-piperazine-1-yl]-ethyl]-cyclohexyl}-N',N'-dimethylurea hydrochloride Form A, B, and C as an active ingredient.

A use of trans-N-{4-[2-[4-(2,3-dichlorophenyl)-piperazine-1-yl]-ethyl]-cyclohexyl}-N',N'-dimethylurea hydrochloride Form A, B and C and a pharmaceutical composition thereof is for the treatment of a dopamine receptor-related disease.

The dopamine receptor-related disease may further include: schizophrenia, affective schizophrenia, mild to moderate cognitive impairment, dementia, mania, paranoid mental disorder and paranoia, dyskinesia, neuroleptic-induced Parkinson's syndrome, depression, anxiety, or drug abuse.

The patents WO2008/139235 disclose the crystalline form I and II of cariprazine hydrochloride, wherein the crystalline forms I and II have poor flowability which will affect on the formulation manufacturing. Cariprazine hydrochloride crystalline forms I and II have difficulty in blending with other excipients due to their poor flowability which will affect the actual amount of each formulation unit. When forming or filling cariprazine hydrochloride tablets, capsules, etc., the powder of API with poor flowability tends to have rough surfaces or easily stick to agglomerates. The poor fluidity of cariprazine hydrochloride also affects the process and increases the cost of the formulation manufacturing. During storage and Transportation of the formulation, formulations made of cariprazine hydrochloride crystalline forms I and II with poorly flowability will be sensitive to environmental temperature, humidity, pressure of mechanical forces, etc., and reduces the stability of the drug and effectiveness. In order to solve the flowability problem of cariprazine hydrochloride crystalline forms I and II, the present invention found the new crystalline form A, B, or C through a large number of polymorphs screening work. Those new forms can significantly improve the flowability of cariprazine hydrochloride which is conducive to the development of pharmaceutical formulations.

DETAILED DESCRIPTION

The specific embodiments of the present invention are further described in detail below with reference to the drawings and embodiments. The following examples are intended to illustrate the invention, but are not intended to limit the scope of the invention.

The X-ray powder diffraction operation and analysis steps in this patent are as follows:

The Rigaku Ultima IV powder diffractometer was used, which irradiated with Cu—K(R) (40 kV, 40 mA) at room temperature using a D/tex Ultra detector. The scanning range is from 3° to 45° in the 2θ interval, and the scanning speed is 20°/min.

Measurement differences associated with X-ray powder diffraction analysis results are produced by a variety of factors including: (a) errors in sample preparation (e.g., sample height), (b) instrument error, (c) calibration differences, (d) operator error (including errors that occur when determining peak position), and (e) properties of the substance (e.g., preferred orientation error). Calibration errors and sample height errors often result in displacement of all peaks in the same direction. When using a flat sampler, small differences in sample height will result in large displacements of the XRPD peak position. Systematic studies have shown that a 1 mm sample height difference can result in a 2θ peak shift of up to 10. These displacements can be identified from the X-ray diffraction pattern and can be eliminated by compensating for the displacement (using a system calibration factor for all peak position values) or recalibrating the instrument. As described above, the measurement errors from different instruments can be corrected by applying a system calibration factor to make the peak positions consistent.

Differential scanning calorimetry (DSC) analysis was performed on the crystal forms in the examples. The operation and analysis steps were as follows. ATA Q2000 differential scanning calorimeter was used, an $N_2$ atmosphere was used, and the heating rate was 10° C./min.

Thermogravimetric (TGA) analysis was performed on the crystal forms in the examples. The operation and analysis steps were as follows. A TA Q500 thermogravimetric analyzer was used, and an $N_2$ atmosphere was used. The heating rate was 10° C./min.

EXAMPLE 1

Slurry or dissolve 50 mg of trans-N-{4-[2-[4-(2,3-dichlorophenyl)-piperazine-1-yl]-ethyl]-cyclohexyl}-N',N'-dimethylurea in 0.5 mL methanol, and then 40 uL concentrated hydrochloric acid to produce a precipitate. The precipitation was allowed to be stirred for 24 hours and the trans-N-{4-[2-[4-(2,3-dichlorophenyl)-piperazine-1-yl]-ethyl]-cyclohexyl}-N',N'-dimethylurea hydrochloride form A was obtained.

Figure 1:
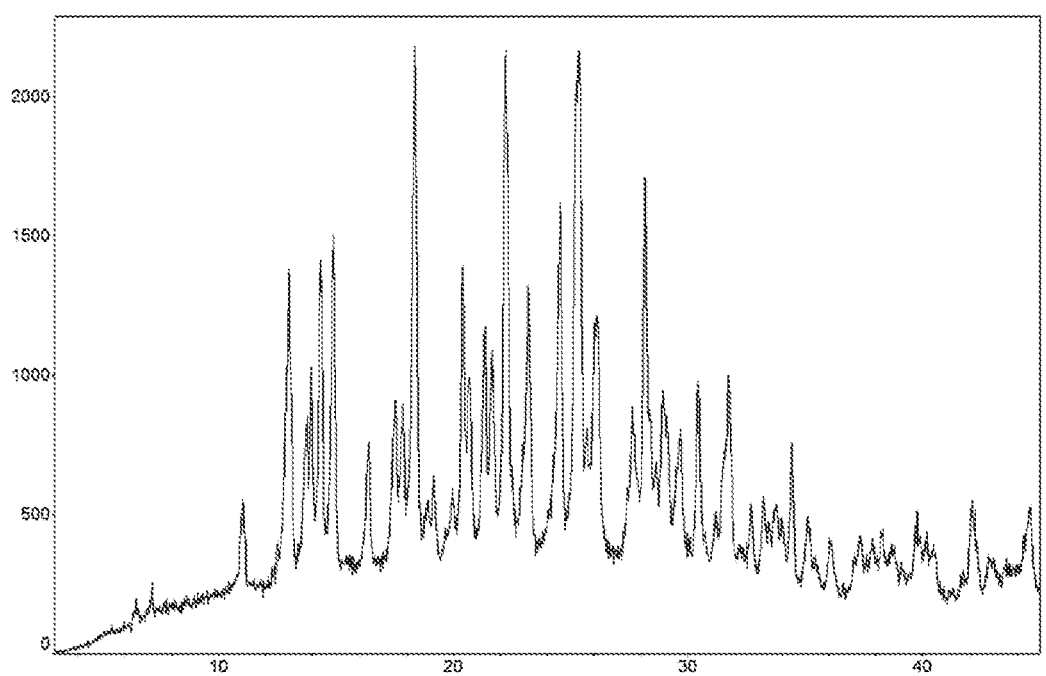
FIG. 1 is an XPRD pattern of trans-N-{4-[2-[4-(2,3-dichlorophenyl)-piperazine-1-yl]-ethyl]-cyclohexyl}-N',N'-dimethylurea hydrochloride Form A. 2θ values in unit of degree in accordance with the abscissa. The intensity of diffraction peak as ordinate.

In the present invention, the trans-N-{4-[2-[4-(2,3-dichlorophenyl)-piperazine-1-yl]-ethyl]-cyclohexyl}-N',N'-dimethylurea hydrochloride Form A, the XRPD patterns are shown in FIG. 1 and the diffraction peaks of the XRPD pattern of Form A are listed in the following table:

| 2-Theta | d(Å) | I(Height)% |
| --- | --- | --- |
| 6.500 | 13.5863 | 4.3 |
| 7.176 | 12.309 | 6.6 |
| 11.039 | 8.0087 | 19.5 |
| 13.000 | 6.8045 | 63.9 |
| 13.743 | 6.4382 | 25.9 |
| 13.959 | 6.339 | 37.6 |
| 14.341 | 6.1709 | 64.5 |
| 14.900 | 5.9406 | 65 |
| 16.400 | 5.4006 | 25.9 |
| 17.541 | 5.0517 | 26.9 |
| 17.861 | 4.962 | 30.4 |
| 18.379 | 4.8232 | 99.8 |
| 18.917 | 4.6874 | 8.2 |
| 19.181 | 4.6235 | 15.2 |
| 19.979 | 4.4404 | 12.6 |
| 20.419 | 4.3458 | 59.3 |
| 20.680 | 4.2914 | 33.5 |
| 21.358 | 4.1569 | 42.3 |
| 21.641 | 4.1031 | 38 |
| 22.239 | 3.994 | 100 |

-continued

| 2-Theta | d(Å) | I(Height)% |
|---|---|---|
| 23.202 | 3.8304 | 53.8 |
| 24.559 | 3.6218 | 68.3 |
| 25.360 | 3.5092 | 99.8 |
| 26.121 | 3.4086 | 36.1 |
| 27.639 | 3.2248 | 21.7 |
| 28.162 | 3.166 | 72.2 |
| 28.940 | 3.0827 | 23.3 |
| 29.699 | 3.0057 | 22.8 |
| 30.422 | 2.9358 | 36.9 |
| 31.182 | 2.866 | 9.8 |
| 31.561 | 2.8324 | 22.8 |
| 31.723 | 2.8183 | 38.7 |
| 32.700 | 2.7363 | 11.7 |
| 33.220 | 2.6947 | 15 |
| 33.780 | 2.6512 | 15.1 |
| 34.002 | 2.6345 | 11.7 |
| 34.438 | 2.6021 | 26.2 |
| 35.100 | 2.5545 | 13.5 |
| 35.441 | 2.5307 | 5.9 |
| 36.058 | 2.4888 | 10.1 |
| 37.098 | 2.4214 | 5.7 |
| 37.338 | 2.4064 | 8.1 |
| 37.857 | 2.3746 | 6.3 |
| 38.226 | 2.3525 | 8.3 |
| 38.795 | 2.3193 | 6 |
| 39.760 | 2.2652 | 15.6 |
| 40.160 | 2.2435 | 12 |
| 40.442 | 2.2285 | 9.5 |
| 41.716 | 2.1634 | 5.1 |
| 42.100 | 2.1445 | 19.9 |
| 42.805 | 2.1108 | 7.1 |
| 43.558 | 2.0761 | 3.9 |
| 44.597 | 2.0301 | 16.9 |

Differential scanning calorimetry (DSC) analysis was performed on the crystal form A in Example 1. The operation and analysis steps were as follows. A TA Q2000 differential scanning calorimeter was used, an $N_2$ atmosphere was used, and the heating rate was 10° C./min. Form A in Example 1 was subjected to thermogravimetric (TGA) analysis. A TA Q500 thermogravimetric analyzer was used, and an $N_2$ atmosphere was used, and the heating rate was 10° C./min.

Figure 2:
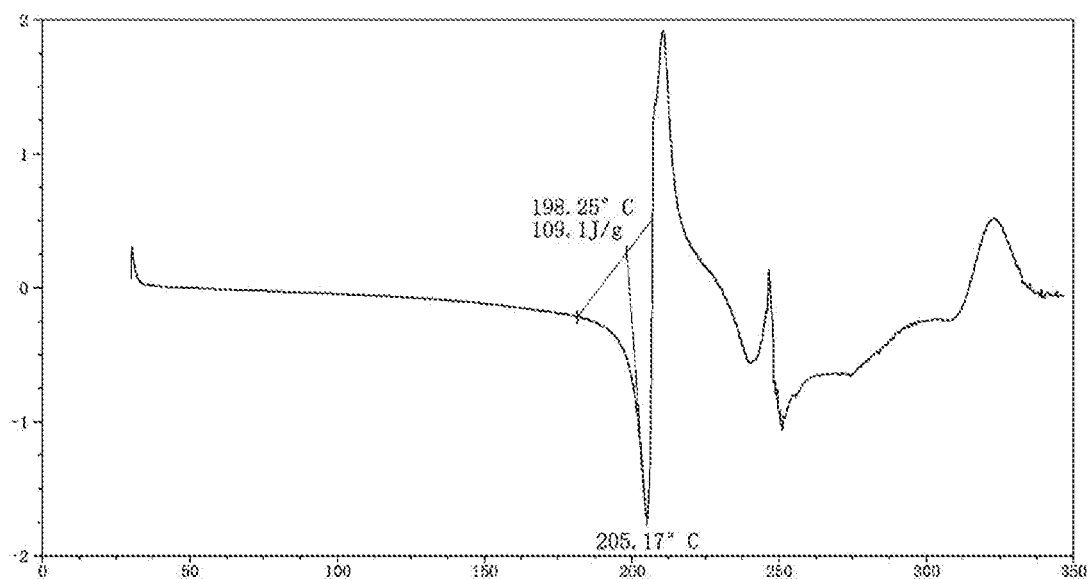
FIG. 2 is a DSC plot of trans-N-{4-[2-[4-(2,3-dichlorophenyl)-piperazine-1-yl]-ethyl]-cyclohexyl}-N',N'-dimethylurea hydrochloride Form A. Temperature in unit of ° C. in accordance with the abscissa. The Heat flow (w/g) as ordinate.
Figure 3:
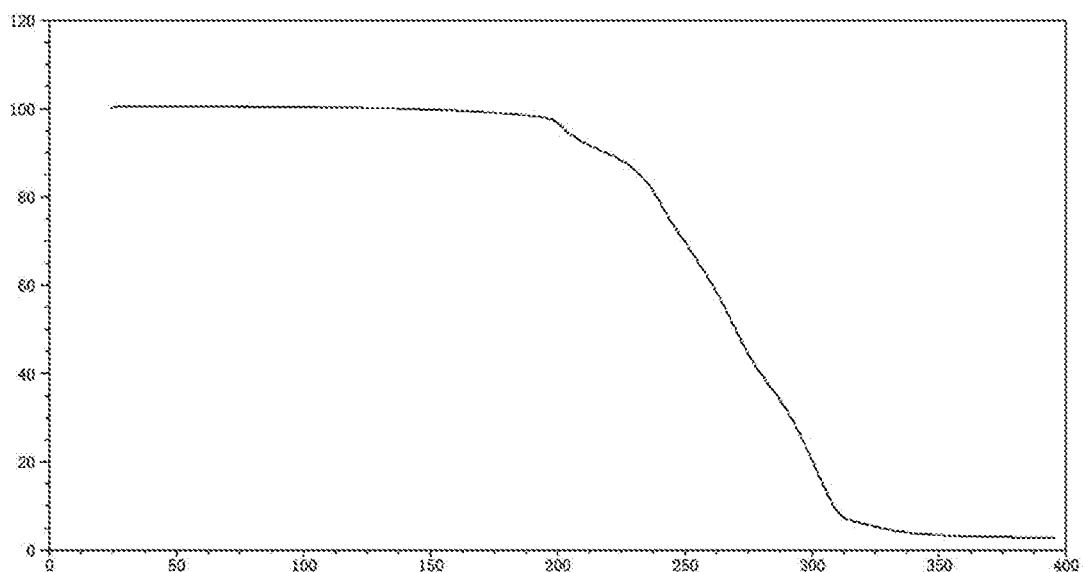
FIG. 3 is a TGA plot of trans-N-{4-[2-[4-(2,3-dichlorophenyl)-piperazine-1-yl]-ethyl]-cyclohexyl}-N',N'-dimethylurea hydrochloride Form A. Temperature in unit of ° C. in accordance with the abscissa. The Weight (%) as ordinate.

The DSC diagram of Form A is shown in FIG. 2, and the TGA diagram of Form A is shown in FIG. 3.

In Example 1, precipitation time for Form A and Forms I and II were compared under pH of simulated intestinal fluid. Take 5 mg of crystal forms A, I and II, and put them in 100-ml glass sample bottles, add 80 mL of pH 6.5 buffer solution (pH value of simulating fasting small intestine), and shake them slightly to observe precipitate. Dissolution status and time of re-precipitation were recorded.

| Crystal Forms | Dissolving time | Precipitate time |
|---|---|---|
| Form I | immediately | 1 min |
| Form II | immediately | 1 min |
| Form A | immediately | 10 min |

From the observation results, it can be known that, compared to Forms I and II, Form A is beneficial to maintaining the dissolved state of cariprazine under near-neutral conditions. Form A has a significantly prolonged maintenance of trans-N-{4-[2-[4-(2,3-dichlorophenyl)-piperazine-1-yl]-ethyl]-cyclohexyl}-N',N'-dimethylurea hydrochloride in the intestinal tract. This will help the drug to be absorbed in the intestine.

EXAMPLE 2

Slurry or dissolve 50 mg of trans-N-{4-[2-[4-(2,3-dichlorophenyl)-piperazine-1-yl]-ethyl]-cyclohexyl}-N',N'-dimethylurea in 0.5 mL isopropanol, and then 40 uL concentrated hydrochloric acid to produce a precipitate. The precipitation was allowed to be stirred for 24 hours and the trans-N-{4-[2-[4-(2,3-dichlorophenyl)-piperazine-1-yl]-ethyl]-cyclohexyl}-N',N'-dimethylurea hydrochloride form A was obtained. The XRPD pattern of crystal form obtained in example 2 is consistent with FIG. 1.

EXAMPLE 3

Slurry or dissolve 50 mg of trans-N-{4-[2-[4-(2,3-dichlorophenyl)-piperazine-1-yl]-ethyl]-cyclohexyl}-N',N'-dimethylurea in 0.5 mL butyl acetate, and then 40 uL concentrated hydrochloric acid to produce a precipitate. The precipitation was allowed to be stirred for 24 hours and the trans-N-{4-[2-[4-(2,3-dichlorophenyl)-piperazine-1-yl]-ethyl]-cyclohexyl}-N',N'-dimethylurea hydrochloride form A was obtained. The XRPD pattern of crystal form obtained in example 3 is consistent with FIG. 1.

EXAMPLE 4

Slurry or dissolve 50 mg of trans-N-{4-[2-[4-(2,3-dichlorophenyl)-piperazine-1-yl]-ethyl]-cyclohexyl}-N',N'-dimethylurea in 0.5 mL N-hexane, and then 40 uL concentrated hydrochloric acid to produce a precipitate. The precipitation was allowed to be stirred for 24 hours and the trans-N-{4-[2-[4-(2,3-dichlorophenyl)-piperazine-1-yl]-ethyl]-cyclohexyl}-N',N'-dimethylurea hydrochloride form A was obtained. The XRPD pattern of crystal form obtained in example 4 is consistent with FIG. 1.

EXAMPLE 5

Figure 4:
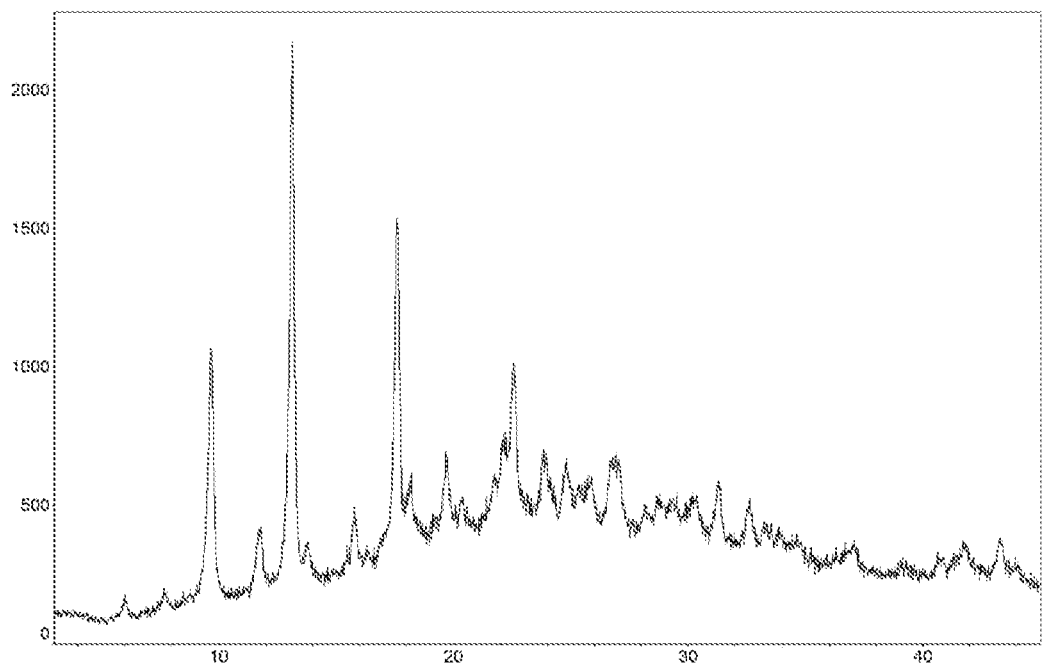
FIG. 4 is an XPRD pattern of trans-N-{4-[2-[4-(2,3-dichlorophenyl)-piperazine-1-yl]-ethyl]-cyclohexyl}-N',N'-dimethylurea hydrochloride Form B. 2θ values in unit of degree in accordance with the abscissa. The intensity of diffraction peak as ordinate.

Slurry or dissolve 50 mg of trans-N-{4-[2-[4-(2,3-dichlorophenyl)-piperazine-1-yl]-ethyl]-cyclohexyl}-N',N'-dimethylurea chloride in 0.5 mL chloroform, and then add hexane drop wise into the solution till precipitate observed. The precipitation was allowed to be stirred for 24 hours and the trans-N-{4-[2-[4-(2,3-dichlorophenyl)-piperazine-1-yl]-ethyl]-cyclohexyl}-N',N'-dimethylurea hydrochloride form B was obtained. The XRPD pattern of crystal form obtained in example 5 is consistent with FIG. 4 and the diffraction peaks of the XRPD pattern of Form B are listed in the following table:

| 2-Theta | d(Å) | I(Height)% |
|---|---|---|
| 9.701 | 9.1096 | 46.3 |
| 11.818 | 7.4821 | 10.7 |
| 13.179 | 6.7125 | 100.0 |
| 15.819 | 5.5976 | 11.2 |
| 17.640 | 5.0236 | 61.0 |
| 18.238 | 4.8602 | 11.3 |
| 19.724 | 4.4974 | 13.9 |
| 22.619 | 3.9278 | 27.0 |
| 23.879 | 3.7233 | 11.7 |
| 24.860 | 3.5786 | 9.4 |
| 27.118 | 3.2856 | 11.5 |
| 31.359 | 2.8502 | 10.3 |
| 32.657 | 2.7398 | 7.3 |

Figure 5:
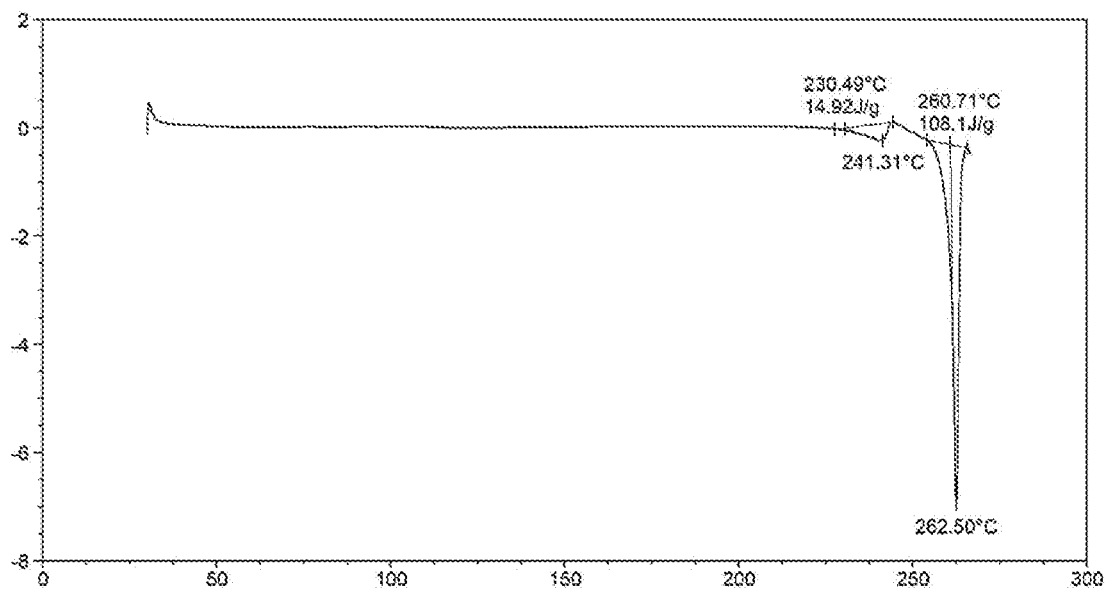
FIG. 5 is a DSC plot of trans-N-{4-[2-[4-(2,3-dichlorophenyl)-piperazine-1-yl]-ethyl]-cyclohexyl}-N',N'-dimethylurea hydrochloride Form B. Temperature in unit of ° C. in accordance with the abscissa. The Heat flow (w/g) as ordinate.
Figure 6:
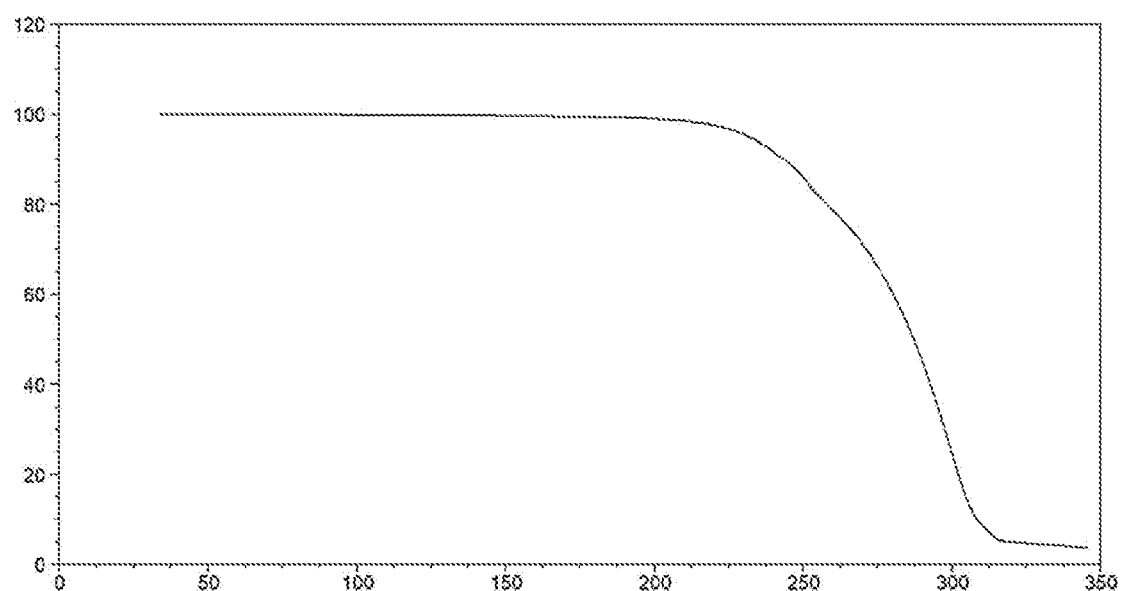
FIG. 6 is a TGA plot of trans-N-{4-[2-[4-(2,3-dichlorophenyl)-piperazine-1-yl]-ethyl]-cyclohexyl}-N',N'-dimethylurea hydrochloride Form B. Temperature in unit of ° C. in accordance with the abscissa. The Weight (%) as ordinate.

The DSC plot of Form B is shown in FIG. 5, and the TGA plot of Form B is shown in FIG. 6.

EXAMPLE 6

Slurry or dissolve 50 mg of trans-N-{4-[2-[4-(2,3-dichlorophenyl)-piperazine-1-yl]-ethyl]-cyclohexyl}-N',N'-dimethylurea chloride in 0.5 mL chloroform, and then add isopropyl ether drop wise into the solution till precipitate observed. The precipitation was allowed to be stirred for 24 hours and the trans-N-{4-[2-[4-(2,3-dichlorophenyl)-piperazine-1-yl]-ethyl]-cyclohexyl}-N',N'-dimethylurea hydrochloride form B was obtained. The XRPD pattern of crystal form obtained in example 6 is consistent with FIG. 4.

EXAMPLE 7

Slurry or dissolve 50 mg of trans-N-{4-[2-[4-(2,3-dichlorophenyl)-piperazine-1-yl]-ethyl]-cyclohexyl}-N',N'-dimethylurea chloride in 0.5 mL ethanol, and then add isopropyl ether drop wise into the solution till precipitate observed. The precipitation was allowed to be stirred for 24 hours and the trans-N-{4-[2-[4-(2,3-dichlorophenyl)-piperazine-1-yl]-ethyl]-cyclohexyl}-N',N'-dimethylurea hydrochloride form B was obtained. The XRPD pattern of crystal form obtained in example 7 is consistent with FIG. 4.

EXAMPLE 8

Figure 7:
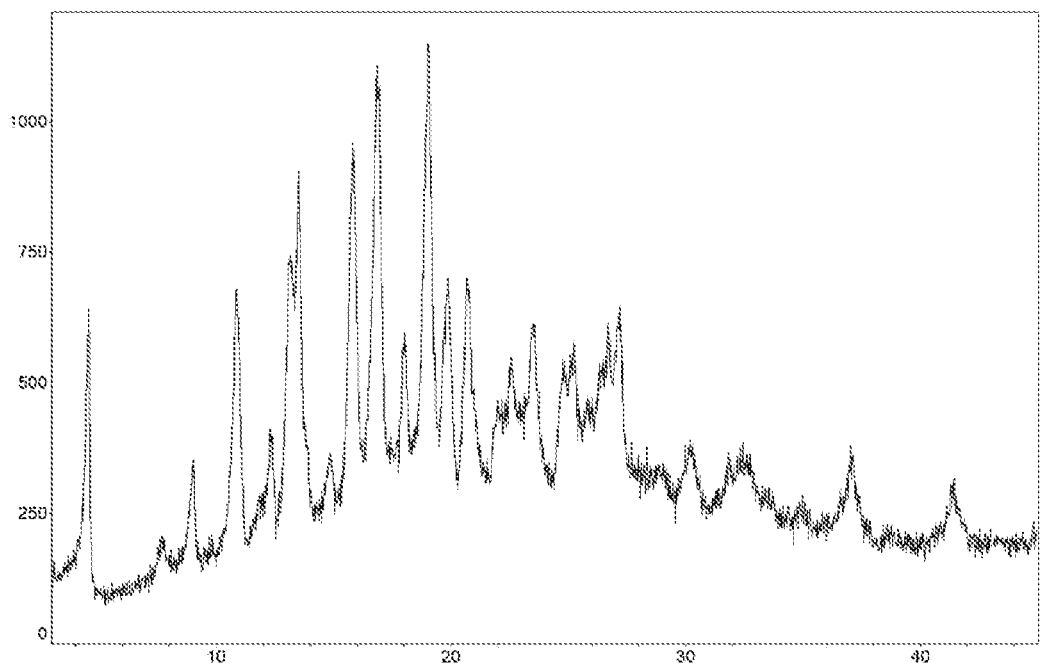
FIG. 7 is an XPRD pattern of trans-N-{4-[2-[4-(2,3-dichlorophenyl)-piperazine-1-yl]-ethyl]-cyclohexyl}-N',N'-dimethylurea hydrochloride Form C. 2θ values in unit of degree in accordance with the abscissa. The intensity of diffraction peak as ordinate.

Slurry or dissolve 50 mg of trans-N-{4-[2-[4-(2,3-dichlorophenyl)-piperazine-1-yl]-ethyl]-cyclohexyl}-N',N'-dimethylurea chloride in 0.5 mL dichloromethane, and then add hexane drop wise into the solution till precipitate observed. The precipitation was allowed to be stirred for 24 hours and the trans-N-{4-[2-[4-(2,3-dichlorophenyl)-piperazine-1-yl]-ethyl]-cyclohexyl}-N',N'-dimethylurea hydrochloride form C was obtained. The XRPD pattern of crystal form obtained in example 8 is consistent with FIG. 7 and the diffraction peaks of the XRPD pattern of Form B are listed in the following table:

| 2-Theta | d(Å) | I(Height)% |
|---|---|---|
| 4.582 | 19.269 | 70.5 |
| 9.077 | 9.7345 | 26.2 |
| 10.919 | 8.096 | 64.5 |
| 12.342 | 7.1654 | 23.4 |
| 13.200 | 6.702 | 66.0 |
| 13.560 | 6.5248 | 86.5 |
| 14.898 | 5.9414 | 11.7 |
| 15.841 | 5.59 | 83.1 |
| 16.881 | 5.2477 | 97.5 |
| 18.061 | 4.9076 | 28.3 |
| 19.080 | 4.6476 | 100.0 |
| 19.920 | 4.4535 | 44.4 |
| 20.703 | 4.2869 | 50.3 |

Figure 8:
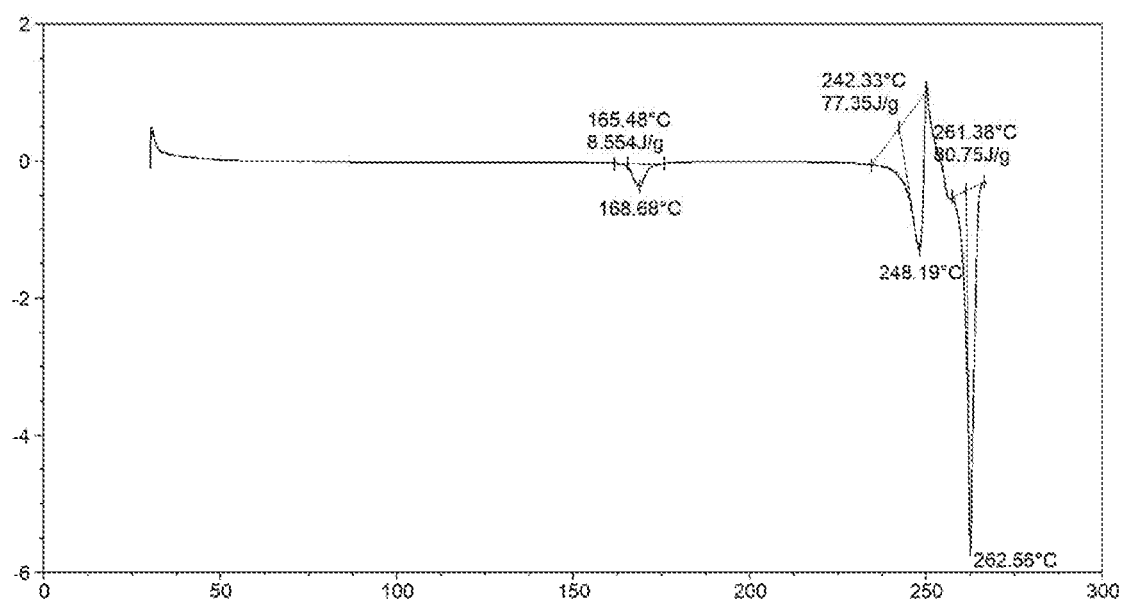
FIG. 8 is a DSC plot of trans-N-{4-[2-[4-(2,3-dichlorophenyl)-piperazine-1-yl]-ethyl]-cyclohexyl}-N',N'-dimethylurea hydrochloride Form C. Temperature in unit of ° C. in accordance with the abscissa. The Heat flow (w/g) as ordinate.
Figure 9:
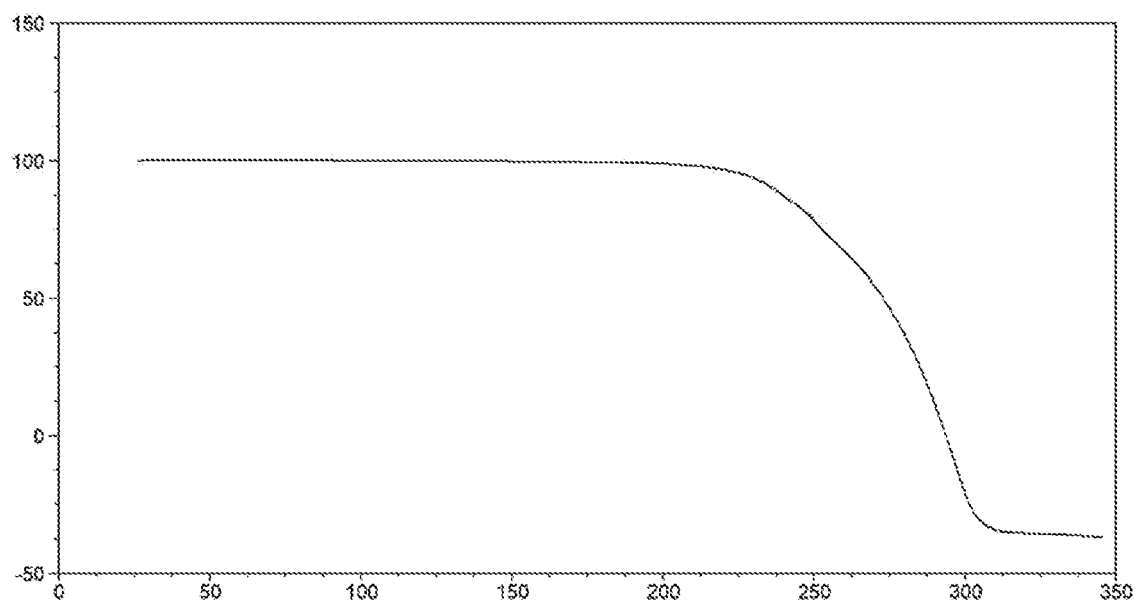
FIG. 9 is a TGA plot of trans-N-{4-[2-[4-(2,3-dichlorophenyl)-piperazine-1-yl]-ethyl]-cyclohexyl}-N',N'-dimethylurea hydrochloride Form C. Temperature in unit of ° C. in accordance with the abscissa. The Weight (%) as ordinate.

The DSC plot of Form C is shown in FIG. 8, and the TGA plot of Form C is shown in FIG. 9.

EXAMPLE 9

Slurry or dissolve 50 mg of trans-N-{4-[2-[4-(2,3-dichlorophenyl)-piperazine-1-yl]-ethyl]-cyclohexyl}-N',N'-dimethylurea chloride in 0.5 mL dichloromethane, and then add isopropyl ether drop wise into the solution till precipitate observed. The precipitation was allowed to be stirred for 24 hours and the trans-N-{4-[2-[4-(2,3-dichlorophenyl)-piperazine-1-yl]-ethyl]-cyclohexyl}-N',N'-dimethylurea hydrochloride form C was obtained. The XRPD pattern of crystal form obtained in example 9 is consistent with FIG. 7.

EXAMPLE 10

Powder flowability test: A petri dish with a diameter of 7 cm in the bottom plate is used. Two glass funnels are staggered on top of each other and fixed on an iron stand. The distance between the lower funnel outlet and the bottom plate is between 3.5-6.0 cm. Take some cariprazine hydrochlorides in different crystal forms, and slowly add them from the upper funnel, so that the sample gradually accumulates on the chassis through the buffer of the two funnels to form a cone until the highest cone is obtained. Measure the height H of the cone. Determine three times for each sample, take the average, and calculate the angle of repose as follows:

$$\alpha = \text{arctg}(H/R)$$

Among them, α is the angle of repose and R is the radius of the chassis.

When the angle of repose of the powder is less than or equal to 30 degrees, it means flowability of powder is good. The flowability requirement in the manufactured process can be satisfied when it is less than or equal to 40 degrees. If the angle of repose of powder is more than 40 degrees, it means flowability is poor.

| Crystal forms of cariprazine HCL | Prepared method | angle of repose |
|---|---|---|
| Form A | Example 1 | 35° |
| Form B | Example 5 | 28° |
| Form C | Example 8 | 31° |
| Form I | WO2008/139235 | 40° |
| Form II | WO2008/139235 | 40° |

Forms A, B, and C of cariprazine hydrochloride significantly improve the flowability of cariprazine hydrochloride in forms of I and II. Forms A, B, and C are more suitable for the drug product manufacturing.

What is claimed is:

1. A crystalline form of trans-N-{4-[2-[4-(2,3-dichlorophenyl)-piperazine-1-yl]-ethyl]-cyclohexyl}-N',N-dimethylurea hydrochloride designated as crystalline form A, having an X-ray powder diffraction pattern comprising diffraction peaks at at least three 2θ value of:
  22.2±0.2, 18.4±0.2, 25.4±0.2, 28.2±0.2, 24.6±0.2, 14.9±0.2, 14.3±0.2, 13.0±0.2, 20.4±0.2, 23.2±0.2, 21.4±0.2, 31.7±0.2, 21.6±0.2, 14.0±0.2, 30.4±0.2, 26.1±0.2, 20.7±0.2, 17.9±0.2, 17.5±0.2, 34.4±0.2, 13.7±0.2, 16.4±0.2, and 28.9±0.2, and having an angle of repose of 35°.

2. A process for the preparation of
  trans-N-{4-[2-[4-(2,3-dichlorophenyl)-piperazine-1-yl]-ethyl]-cyclohexyl}-N',N-dim ethylurea hydrochloride Form A according to claim 1 comprising:
  (i) dissolving trans-N-{4-[2-[4-(2,3-dichlorophenyl)-piperazine-1-yl]-ethyl]-cyclohexyl}-N',N-dim ethylurea free base in an organic solution, wherein the organic solvent is selected from the group consisting of methanol, isopropanol, butyl acetate, n-hexane, acetonitrile, acetone, methyl ethyl ketone, 4-methyl-2-pentanone, diethyl ether, isopropyl ether, methyl tert-butyl ether, toluene, P-xylene, 1,2-dichloroethane, 1,4-dioxane, tetrahydrofuran, trifluorotoluene, cumene, mesitylene, chlorobenzene, n-butyl ether, methylcyclopentyl ether, phenyl ether, 2-nitropropane, dimethyl carbonate, ethyl formate, 2-methyltetrahydrofuran, or ethylene glycol diethyl ether;

(ii) adding hydrochloride acid into the solution prepared in the step (i) to precipitate a trans-N-{4-[2-[4-(2,3-dichlorophenyl)-piperazine-1-yl]-ethyl]-cyclohexyl}-N',N-dim ethylurea chloride salt; and (iii) obtaining trans-N-{4-[2-[4-(2,3-dichlorophenyl)-piperazine-1-yl]-ethyl]-cyclohexyl}-N',N-dim ethylurea hydrochloride Form A after liquid-solid separation.

3. A crystalline form of trans-N-{4-[2-[4-(2,3-dichlorophenyl)-piperazine-1-yl]-ethyl]-cyclohexyl}-N',N-dimethylurea hydrochloride designated as crystalline form A, having an X-ray powder diffraction pattern comprising diffraction peaks at at least three 2θ value of:

13.2±0.2, 17.6±0.2, 9.7±0.2, 22.6±0.2, 19.7±0.2, 23.9±0.2, 27.1±0.2, 18.2±0.2, 15.8±0.2, 11.8±0.2, 31.4±0.2, 24.9±0.2, and 32.7±0.2, and having an angle of repose of 28°.

4. A process for the preparation of trans-N-{4-[2-[4-(2,3-dichlorophenyl)-piperazine-1-yl]-ethyl]-cyclohexyl}-N',N-dim ethylurea hydrochloride Form B according to claim 3 comprising:

(i) dissolving trans-N-{4-[2-[4-(2,3-dichlorophenyl)-piperazine-1-yl]-ethyl]-cyclohexyl}-N',N-dim ethylurea hydrochloride in an organic solution, wherein the organic solvent is selected from the group consisting of chloroform or ethanol;

(ii) adding antisolvent (solvent has low solubility to the compound) into the solution prepared in step (i), wherein the antisolvent was selected from N-heptane or isopropyl ether; and (iii) obtaining trans-N-{4-[2-[4-(2,3-dichlorophenyl)-piperazine-1-yl]-ethyl]-cyclohexyl}-N',N-dim ethylurea hydrochloride Form B after liquid-solid separation.

5. A crystalline form of trans-N-{4-[2-[4-(2,3-dichlorophenyl)-piperazine-1-yl]-ethyl]-cyclohexyl}-N',N-dimethylurea hydrochloride designated as crystalline form A, having an X-ray powder diffraction pattern comprising diffraction peaks at at least three 2θ value of:

19.1±0.2, 16.9±0.2, 13.6±0.2, 15.8±0.2, 4.6±0.2, 13.2±0.2, 10.9±0.2, 20.7±0.2, 19.9±0.2, 18.1±0.2, 9.1±0.2, 12.3±0.2, and 14.9±0.2, and having an angle of repose of 31°.

6. A process for the preparation of trans-N-{4-[2-[4-(2,3-dichlorophenyl)-piperazine-1-yl]-ethyl]-cyclohexyl}-N',N-dim ethylurea hydrochloride Form C according to claim 5 comprising:

(i) dissolving trans-N-{4-[2-[4-(2,3-dichlorophenyl)-piperazine-1-yl]-ethyl]-cyclohexyl}-N',N-dimeth ylurea hydrochloride salt in an organic solution, wherein the organic solvent is selected from the group consisting of dichloromethane;

(ii) adding antisolvent (solvent has low solubility to the compound) into the solution prepared in step (i), wherein the antisolvent was selected from N-heptane or isopropyl ether; and (iii) obtaining trans-N-{4-[2-[4-(2,3-dichlorophenyl)-piperazine-1-yl]-ethyl]-cyclohexyl}-N',N-dim ethylurea hydrochloride Form C after liquid-solid separation.

7. A pharmaceutical composition comprise trans-N-{4-[2-[4-(2,3-dichlorophenyl)-piperazine-1-yl]-ethyl]-cyclohexyl}-N',N-dim ethylurea hydrochloride Form A according to claim 1 as an active ingredient to treat schizophrenia, affective schizophrenia, mild to moderate cognitive impairment, dementia, mania, paranoid mental disorder and paranoia, dyskinesia, neuroleptic-induced Parkinson's syndrome, depression, anxiety, or drug abuse.

8. A pharmaceutical composition comprise trans-N-{4-[2-[4-(2,3-dichlorophenyl)-piperazine-1-yl]-ethyl]-cyclohexyl}-N',N-dim ethylurea hydrochloride Form B according to claim 3 as an active ingredient to treat schizophrenia, affective schizophrenia, mild to moderate cognitive impairment, dementia, mania, paranoid mental disorder and paranoia, dyskinesia, neuroleptic-induced Parkinson's syndrome, depression, anxiety, or drug abuse.

9. A pharmaceutical composition comprise trans-N-{4-[2-[4-(2,3-dichlorophenyl)-piperazine-1-yl]-ethyl]-cyclohexyl}-N',N-dim ethylurea hydrochloride Form C according to claim 5 as an active ingredient to treat schizophrenia, affective schizophrenia, mild to moderate cognitive impairment, dementia, mania, paranoid mental disorder and paranoia, dyskinesia, neuroleptic-induced Parkinson's syndrome, depression, anxiety, or drug abuse.

* * * * *